(12) United States Patent
Gdanski et al.

(10) Patent No.: US 7,472,748 B2
(45) Date of Patent: Jan. 6, 2009

(54) METHODS FOR ESTIMATING PROPERTIES OF A SUBTERRANEAN FORMATION AND/OR A FRACTURE THEREIN

(75) Inventors: Rick D. Gdanski, Duncan, OK (US); Jimmie D. Weaver, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 24 days.

(21) Appl. No.: 11/607,254

(22) Filed: Dec. 1, 2006

(65) Prior Publication Data

US 2008/0133193 A1 Jun. 5, 2008

(51) Int. Cl.
*E21B 49/08* (2006.01)
(52) U.S. Cl. .............. 166/250.1; 166/250.12; 166/264; 166/308.1; 703/10
(58) Field of Classification Search ............. None
See application file for complete search history.

(56) References Cited

U.S. PATENT DOCUMENTS

| | | | | |
|---|---|---|---|---|
| 4,316,810 | A | 2/1982 | Burnham | 252/8.55 R |
| 4,553,601 | A | 11/1985 | Almond et al. | 166/308 |
| 4,627,495 | A | 12/1986 | Harris et al. | 166/280 |
| 5,582,249 | A | 12/1996 | Caveny et al. | 166/276 |
| 5,697,440 | A | 12/1997 | Weaver et al. | 166/281 |
| 5,775,425 | A | 7/1998 | Weaver et al. | 166/276 |
| 5,839,510 | A | 11/1998 | Weaver et al. | 166/276 |
| 5,924,488 | A | 7/1999 | Nguyen et al. | 166/280 |
| 6,076,046 | A * | 6/2000 | Vasudevan et al. | 702/12 |
| 6,691,037 | B1 * | 2/2004 | Poe et al. | 702/13 |
| 6,691,780 | B2 | 2/2004 | Nguyen et al. | 166/254.1 |
| 6,725,926 | B2 | 4/2004 | Nguyen et al. | 166/254.1 |
| 6,766,817 | B2 | 7/2004 | da Silva | |
| 6,918,404 | B2 | 7/2005 | Dias da Silva | |
| 7,066,586 | B2 | 6/2006 | da Silva | |
| 7,244,398 | B2 | 7/2007 | Kotary et al. | |
| 7,285,255 | B2 | 10/2007 | Kadlec et al. | |
| 7,322,402 | B2 | 1/2008 | Hsu | |
| 2007/0212281 | A1 | 9/2007 | Kadlec et al. | |
| 2008/0015531 | A1 | 1/2008 | Bryn et al. | |
| 2008/0019865 | A1 | 1/2008 | Kadlec et al. | |

OTHER PUBLICATIONS

Gdanski, et al., "A new Model for Matching Fracturing Fluid Flowback Composition," Society of Petroleum Engineers, SPE 106040, pp. 1-9, Jan. 29-31, 2007.
Gdanski, et al., "Fracture Face Skin Evolution During CleanUp," Society of Petroleum Engineers, SPE 101083, Sep. 2006.
Gdanski, et al., "Modeling Acid Returns Profiles After HF Acidizing Treatments," Society of Petroleum Engineers, SPE 65035, Feb. 2001.
K. Aziz and A. Settari, "Petroleum Reservoir Simulation," Blitzprint, Ltd., Calgary, Alberta, Canada, 1979.

* cited by examiner

*Primary Examiner*—Zakiya W. Bates
(74) *Attorney, Agent, or Firm*—Robert A. Kent; Baker Botts LLC

(57) ABSTRACT

Methods that include a method of determining one or more approximate properties of a subterranean formation and/or a fracture therein comprising: obtaining fluid identity data for a plurality of flowback fluid samples; and using a reservoir model, with the fluid identity data and one or more subterranean formation properties as inputs thereto, to estimate one or more properties in a subterranean formation. Additional methods are provided.

20 Claims, 8 Drawing Sheets

METHODS FOR ESTIMATING PROPERTIES OF A SUBTERRANEAN FORMATION AND/OR A FRACTURE THEREIN

BACKGROUND

The present invention generally relates to the field of oil and gas subsurface earth formation evaluation techniques and more particularly, to methods for estimating a property of a subterranean formation and/or a property of a fracture in a subterranean formation.

Production of hydrocarbons from a subterranean formation may be affected by a number of factors including pressure, porosity, permeability, permeability functions such as relative permeabilities to water, oil, and gas, reservoir thickness and extent, water saturation, capillary pressure and capillary pressure functions. Generally, to increase production from a well bore and/or to facilitate the flow of hydrocarbons from a subterranean formation, stimulation treatment operations, such as hydraulic fracturing, may be performed.

Hydraulic fracturing typically involves introducing a high pressure fluid into the formation to create and/or enhance fractures that penetrate into the subterranean formation. These fractures can create flow channels to improve the productivity of the well. Generally, once a hydraulic fracture is induced and propagated, the release of pressure will result in the fracture closing and not maintaining a highly conductive passageway for hydrocarbon production. Thus, propping agents or "proppants" of various kinds, chemical or physical, may be used to hold the fractures open and to prevent the closing of the fractures after the fracturing pressure is released. The degree of production enhancement after such a stimulation treatment is dependant on, inter alia, the effective structure of the fracture including the height, width, and length of the fracture, as well as the conductivity of the proppant within the fracture. However, the actual structure of a fracture that is created or enhanced after such a stimulation treatment is generally not known and can only be estimated.

Various methods have been developed to attempt to estimate subterranean formation properties and/or the structure of a fracture resulting from a stimulation operation. One example of a method for estimating such properties is a pressure build-up analysis. Pressure build-up analysis refers to the analysis of data obtained from measurements of the bottomhole pressure in a well that has been shut-in after a flow period. While production of the well is stopped (e.g., for several days), the pressure build-up over time at the well is recorded. A profile of pressure against time may be created and used with mathematical reservoir models to assess the extent and characteristics of the subterranean formation and the near-wellbore area. However, to obtain such data, production from the well must generally be stopped for a significant length of time, which may be undesirable due to the associated expenses of stopping production from a well.

Another example of a method for estimating subterranean formation properties and/or the structure of a fracture resulting from a stimulation operation uses production history matching. Production history matching refers to the process of adjusting unknown parameters of a reservoir model until the model resembles the past production of the reservoir as closely as possible. Similarly, another method utilizes matching treating pressures during the fracturing treatment. When utilizing these matching methods, the accuracy of the matching depends, inter alia, on the quality of the reservoir model and the quality and quantity of pressure and production data. Once a model has been matched, it may be used to simulate future reservoir behavior.

A disadvantage associated with these methods, however, is that several different possible structures of a fracture or characteristics of a subterranean formation may yield the same result. That is, there are many possible solutions, or sets of parameter values, that can likely produce a possible match unless further constraining information is obtained.

SUMMARY

The present invention generally relates to the field of oil and gas subsurface earth formation evaluation techniques and more particularly, to methods for estimating a property of a subterranean formation and/or a property of a fracture in a subterranean formation.

In one embodiment, the present invention provides a method that comprises introducing a fracturing fluid into at least a portion of a subterranean formation at a pressure sufficient to create or enhance a fracture therein; recovering a plurality of flowback fluid samples from the subterranean formation over time; determining fluid identity data for the fracturing fluid and for one or more of the flowback fluid samples; and determining one or more approximate properties of the subterranean formation and/or fracture based, at least in part, on the fluid identity data, one or more subterranean formation properties, and at least one reservoir model.

In another embodiment, the present invention provides a method comprising recovering a plurality of flowback fluid samples from a subterranean formation over time; determining fluid identity data for one or more of the flowback fluid samples; and determining one or more approximate properties of the subterranean formation and/or a fracture therein based, at least in part, on the fluid identity data, one or more subterranean formation properties, and at least one reservoir model.

In another embodiment, the present invention provides a method of determining one or more approximate properties of a subterranean formation and/or a fracture therein comprising obtaining fluid identity data for a plurality of flowback fluid samples; and using a reservoir model, with the fluid identity data and one or more subterranean formation properties as inputs thereto, to estimate one or more properties in a subterranean formation.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

Figure 1:
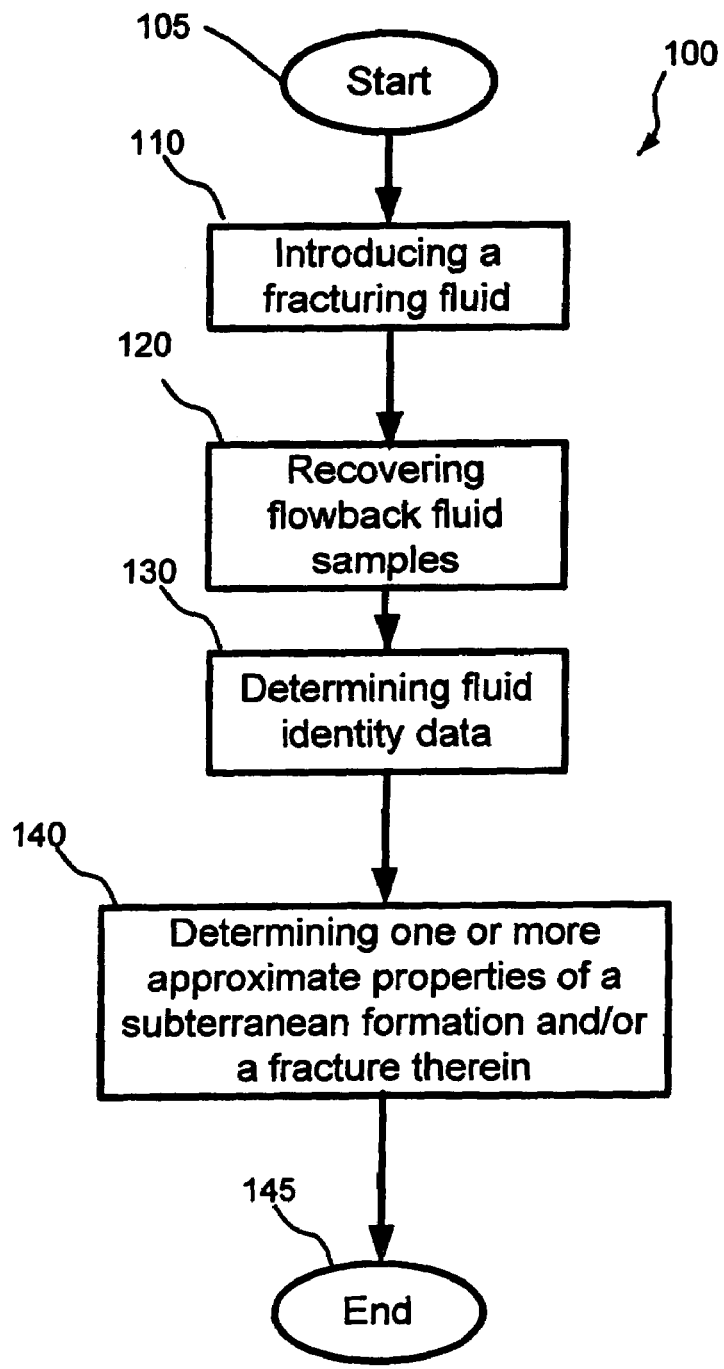
FIG. 1 is a flow chart illustrating one embodiment of a method for determining a property of a subterranean formation and/or a property of a fracture in a subterranean formation.

The present invention generally relates to the field of oil and gas subsurface earth formation evaluation techniques and more particularly, to methods for estimating a property of a subterranean formation and/or a property of a fracture in a subterranean formation.

Methods of the present invention may be useful for estimating a property of a subterranean formation including, but not limited to, relative permeability functions and capillary pressure functions, as well as a property of a fracture including, but not limited to, effective fracture length, fracture conductivity, and fracture porosity. In addition, the methods of the present invention may be used, in conjunction with previously determined information regarding the subterranean formation, to infer the ratio of productive surface area of a fracture to the created surface area of a fracture, the created fracture length, and fracture width. In some embodiments, the methods of the present invention may be used to evaluate the efficacy of a stimulation treatment and/or the resulting clean-up after a stimulation treatment. Additionally, in some embodiments, the methods of the present invention may be useful in evaluating the interactions of a component in a stimulation treatment fluid with the subterranean formation.

One of the many advantages of the methods of the present invention is that more constrained information about the subterranean formation and/or a fracture therein can be obtained because the methods generally utilize the compositions of flowback fluids returned to the surface after a fracturing treatment in conjunction with a reservoir model to estimate a property of the subterranean formation and/or a property of a fracture in a subterranean formation. Similarly, when used in conjunction with previously determined information regarding the subterranean formation, the possibilities of the structure of a fracture and/or characteristics of the subterranean formation may be further narrowed. Thus, a more unique solution regarding the characteristics of the subterranean formation and/or fracture therein may be obtained.

In accordance with the methods of the present invention, a fracturing fluid may be introduced into a subterranean formation at a pressure sufficient to create or enhance a fracture therein. Any known fracturing fluids/techniques are suitable for use in conjunction with the present invention. The fracturing fluid, preferably, may be of a different composition than the formation fluid, or may comprise a tracer, so that it may be differentiated from the formation fluid upon production. The term "tracer" as used herein generally refers to a marker that is present in the continuous phase of a fluid or incorporated into a coating of a proppant, that may be used to identify an item in a return flow in a desirable manner. Subsequently, a flowback fluid, which may comprise a fracturing fluid, a formation fluid, gas, an analyte and/or a combination thereof, may be produced from the subterranean formation and one or more flowback fluid samples may be collected. The term "flowback fluid samples" as used herein generally refers to samples of a flowback fluid that are collected as a function of time and cumulative volume. Fluid identity data for one or more of the flowback fluid samples may then be determined. The term "fluid identity data" as used herein generally refers to information regarding the presence, absence, and/or concentration of a selected analyte in a flowback fluid sample, as well as information regarding the presence, absence, and/or concentration of a selected analyte in a fracturing fluid introduced into the subterranean formation. The fluid identity data may then be input into a reservoir model, such as a numerical reservoir simulator, along with previously determined information regarding the subterranean formation, to provide an estimate of one or more properties in a subterranean formation and/or one or more properties of a fracture in a subterranean formation.

Generally, the methods of the present invention may relate the amount and/or composition of a fracturing fluid recovered from the subterranean formation to the total amount and/or composition of recovered fluid. In some embodiments, the methods of the present invention also may relate the amount and/or composition of recovered fluids to the time at which the fluid was recovered. The term "recovered fluid" as used herein generally refers to any fluid from a subterranean formation, including, but not limited to, a fracturing fluid, a formation fluid, gas, and/or a combination thereof. This information may then be used to estimate the properties of a fracture including, but not limited to, effective fracture length, fracture conductivity, and/or fracture porosity, and properties of the subterranean formation including, but not limited to, relative permeability functions and capillary pressure functions. In addition, the methods of the present invention may relate the amount and/or composition of a fracturing fluid introduced into the subterranean formation to the total amount and/or composition of recovered fluid. This information may then be used to estimate the efficacy of a fracturing treatment and/or the resulting clean-up after a fracturing treatment.

FIG. 1 shows an example of an implementation of the methods of the present invention. Method 100 generally begins at step 105. In step 110, a fracturing fluid is introduced into at least a portion of a subterranean formation at a pressure sufficient to create or enhance a fracture therein. Any fracturing fluid known in the art may be suitable for use in the methods of the present invention, including aqueous based fracturing fluids and hydrocarbon based fracturing fluids. However, it is generally desirable that the fracturing fluid be distinguishable in some way from the formation fluid. In some instances, a hydrocarbon based fracturing fluid may be useful if it is capable of being differentiated from hydrocarbons produced from the formation. Similarly, an aqueous based fracturing fluid may be useful if it is capable of being differentiated from formation water.

Examples of fracturing fluids that may be suitable for use in the present invention include, but are not limited to, aqueous fracturing fluids, hydrocarbon-based fracturing fluids, viscosified treatment fluids, aqueous gels, emulsions, foamed fracturing fluids, and other suitable fracturing fluids. Where used, the aqueous gels are generally comprised of water and one or more gelling agents. Where used, the emulsions may be comprised of two or more immiscible liquids such as an aqueous gelled liquid and a hydrocarbon-based fluid. Also, where used, the foams may be comprised of two or more immiscible liquids such as an aqueous gelled liquid and a liquified, normally gaseous fluid, such as nitrogen. In one embodiment, the fracturing fluid may be an aqueous gel comprised of water, a gelling agent for gelling the water and increasing its viscosity, and optionally, a cross-linking agent for cross-linking the gel and further increasing the viscosity of the fluid. The increased viscosity of the gelled or gelled and cross-linked fracturing fluid, inter alia, reduces fluid loss and allows the fracturing fluid to transport suspended proppant. The fracturing fluids may also include one or more of a variety of well-known additives such as breakers, stabilizers, fluid loss control additives, clay stabilizers, bactericides, and the like. Other examples of fracturing fluids suitable for use in the methods of present invention include those described in U.S. Pat. Nos. 4,627,495, 4,553,601 and 4,316,810, the relevant disclosures of which are incorporated herein by reference.

In one embodiment, the fracturing fluid may comprise a tracer that may allow the fracturing fluid to be differentiated from formation fluids. In another embodiment, a fracturing fluid may comprise one or more tracers in separate portions of the fracturing fluid so that upon production of the fracturing fluid, information may be gleaned regarding which portion of a fracture is conductive. In another embodiment, a fracturing fluid may comprise one or more tracers that may preferentially interact with certain minerals present in the subterranean formation. The presence or absence of these tracers in the flowback fluid samples may then be used to quantify the presence or absence of such minerals. For example, in one embodiment, a fracturing fluid used in the methods of the present invention may comprise a chemical that preferentially adsorbs into smectite clay, such as polycationic materials. After obtaining fluid identity data from the flowback fluid samples, an absence or presence of the chemical in the flowback fluid sample may then indicate the presence or absence of smectite clay. Examples of tracers that may be suitable for use in the methods of the present invention include, but are not limited to, dyes, such as flourescein dyes, oil soluble dyes, and oil dispersible dyes; organic materials, such as guar, sugars, glycerol, surfactants, scale inhibitors, etc.; phosphorescent pigments; fluorescent pigments; photoluminescent pigments; oil dispersible pigments; radioactive materials; metals; salts; those described in U.S. Pat. Nos. 6,725,926 and 6,691,780, the relevant disclosures of which are incorporated herein by reference, and combinations and derivatives thereof.

Optionally, in some embodiments the fracturing fluid may comprise proppant. A wide variety of proppant may be used in accordance with the present invention, including, but not limited to, sand, bauxite, ceramic materials, glass materials, resin precoated proppant (e.g., commercially available from Borden Chemicals and Santrol, for example, both from Houston, Tex.), polymer materials, "TEFLON™" (tetrafluoroethylene) materials, nut shells, ground or crushed nut shells, seed shells, ground or crushed seed shells, fruit pit pieces, ground or crushed fruit pits, processed wood, composite particulates prepared from a binder with filler particulate including silica, alumina, fumed carbon, carbon black, graphite, mica, titanium dioxide, meta-silicate, calcium silicate, kaolin, talc, zirconia, boron, fly ash, hollow glass microspheres, and solid glass; or mixtures thereof. Other types of proppants may be suitable as well. The proppants may be coated with resins, tackifiers, or any other suitable coating if desired that may allow for enhanced agglomeration downhole. Examples of proppants that may be suitable for use in the methods of the present invention include, but are not limited to, those described in U.S. Pat. Nos. 5,582,249, 5,697,440, 5,775,425, 5,839,510, and 5,924,488, the relevant disclosures of which are incorporated herein by reference. In some embodiments, the proppant used may have a particle size in the range of from about 2 to about 400 mesh, U.S. Sieve Series.

In some embodiments, the proppant may further comprise a coating (e.g., a degradable polymeric coating, resin coating, etc.) that comprises one or more tracers. It is believed that if proppant comprising a tracer comes into contact with a formation fluid, then the tracer may be released and produced with the flowback fluid sample. Fluid identity data may then be utilized to identify which portions of a propped fracture are conductive and to further constrain an estimate of a property of a fracture.

In another embodiment, a tracer may be incorporated into a portion of a fracturing fluid to specifically adsorb and treat a created fracture face in a particular zone of the subterranean formation. The term "fracture face" as used herein generally refers to a new mineral surface that may be created or exposed in the course of a fracturing treatment. Fluid identity data obtained from a flowback fluid sample may then provide information on the amount of fracture face exposed to fluid flow.

In some embodiments, different tracers may be placed in different zones of the formation. In this way, information about specific areas within the formation may be obtained relative to other areas.

After introducing a fracturing fluid into the subterranean formation in step 110, production may be initiated from the subterranean formation and flowback fluid samples may be collected in step 120. The flowback fluid samples may comprise a fracturing fluid, a formation fluid, gas, an analyte, and/or a combination thereof. The flowback fluid samples preferably are collected over time, and analyzed as a function of time and cumulative volume to obtain production data. The volume of flowback fluid recovered in relation to the time it was recovered may be used to determine a production rate of the flowback fluids or conversely, the production rate of the flowback fluids may be used to determine cumulative volume.

In step 130, fluid identity data may be determined for one or more of the flowback fluid samples. In one embodiment, determining fluid identity data may comprise analyzing a fluid flowback sample to determine the presence, absence, and/or concentration of an analyte. Determining fluid identity data may also comprise analyzing a fracturing fluid to be introduced into the subterranean formation to determine the presence, absence, and/or concentration of an analyte. The fluid identity data for the fracturing fluid that is introduced into the subterranean formation may be determined at any time. In some embodiments, it may not be necessary to analyze the fracturing fluid that will be introduced into the subterranean formation to determine its fluid identity data if this data is already available from an alternative source, e.g., a manufacturer's list of the composition of the fracturing fluid.

Examples of suitable analytes may include any ion, chemical, metal, soluble material, organic material, tracer, and/or a combination or derivative thereof that is capable of being identified in a flowback fluid sample. Additionally, suitable analytes may comprise any substance present in a fracturing fluid that may enable it to be differentiated from the formation fluid and/or any substance present in a formation fluid that may enable it to be differentiated from a fracturing fluid. More specifically, examples of suitable analytes include, but are not limited to, ions such as sodium, potassium, chloride, calcium, magnesium, iron, sulfate, barium, boron, etc.; carbohydrates; other chemicals such as gelling agents, crosslinkers, breakers, surfactants, etc; and/or tracers. One of ordinary skill in the art with the benefit of this disclosure will be able to recognize additional analytes suitable for use in the methods of the present invention.

In some embodiments, analyzing a fluid flowback sample and/or fracturing fluid to determine the presence, absence, and/or concentration of an analyte may involve atomic absorption spectroscopy (AA), which may be useful in determining fluid identity data regarding the presence, absence, and/or concentration of a metal; inductively coupled plasma emission spectroscopy, which may be useful in determining fluid identity data regarding the presence, absence, and/or concentration of a cation, such as a metal and/or salt; silver nitrate titration, which may be useful in determining fluid identity data regarding the presence, absence, and/or concentration of chloride; spectroscopic techniques, such as infrared, nuclear magnetic resonance, ultraviolet, x-ray, and visible spectroscopies, which may be useful in determining fluid identity data regarding the presence, absence, and/or concentration of a dye, organic material, or other suitable analytes; ion chromatography, which may be useful in determining fluid identity data regarding the presence, absence, and/or concentration of an ion; and gas chromatography, which may be useful in determining fluid identity data regarding the presence, absence, and/or concentration of several different analytes including carbohydrates; chemicals such as gelling agents, crosslinkers, breakers, surfactants, etc; and/or tracers. Other techniques may be suitable as well as recognized by those skilled in the art. The most appropriate technique preferably should be selected so as to provide the most accurate information about the desired analyte. One of ordinary skill in the art with the benefit of this disclosure will be able to recognize a suitable method for determining the presence, absence, and/or concentration of a desired analyte.

After obtaining the fluid identity data, the data may be input into a reservoir model, in step 140, to determine one or more approximate properties of the subterranean formation and/or one or more approximate properties of a fracture in the subterranean formation. Additional data including, but not limited to, the production rate of the flowback fluid and previously determined data regarding the subterranean formation may also be used as input for the reservoir model. Previously determined data regarding the subterranean formation may be any data that provides physical information regarding a property of the subterranean formation and/or a property of a fracture in the subterranean formation. Examples of previously determined data may include, inter alia, initial reservoir pressure, reservoir temperature, gas viscosity, gas density, gas gravity, water viscosity, matrix porosity, matrix permeability, water saturation, well spacing, fracture height, fracture porosity, formation fluid composition, fracturing fluid composition, fracturing fluid volume, initial invasion water saturation, initial propped fracture water saturation, initial wellbore node water saturation, etc.

Examples of methods of obtaining such data include, but are not limited to, laboratory testing of subterranean fluids and/or core samples, logging techniques, seismic techniques, pressure transient analysis, and reservoir modeling based on production matching and/or pressure matching.

While the methods of present invention do not require that previously determined data be used, the estimates of properties of the subterranean formation and/or properties of a fracture in a subterranean formation will generally be more accurate if more data regarding the subterranean formation is known. In some embodiments, it may be particularly desirable to know the bottom hole flowing pressure to further constrain possible estimates.

Examples of reservoir modeling methods suitable for use in the methods of the present invention include, but are not limited to, reservoir models such as numerical reservoir simulators. In one embodiment, the fluid identity data may be input into a numerical reservoir simulator that is a two dimensional model that utilizes a backward difference scheme using upstream transmissibilities and the simultaneous solution method. The simulator models ¼ of a square reservoir using a grid block with a well at the center and a symmetrical fracture with two wings. Examples of numerical reservoir simulators that may be suitable for use in the present invention are described in "Petroleum Reservoir Simulation" by K. Aziz and A. Settari, Blitzprint, Ltd., Calgary, Alberta, Canada (1979), and Gdanski, et al., *Fracture Face Skin Evolution During Cleanup*, paper SPE 101083 (2006), the relevant disclosures of which are herein incorporated by reference.

During step 140, fluid identity data; production data, including the production rate of the flowback fluid; and previously determined data regarding the subterranean formation may be input into the reservoir model. In addition, initial estimated values for the unknown parameters of the subterranean formation, which may include, inter alia, capillary pressure, relative permeability, and certain fracture properties such as effective fracture length, productive surface area of a fracture, fracture conductivity, fracture width, fracture porosity, and fracture height are also input into the reservoir model.

Based on this input, the reservoir model then produces predicted production data and predicted flowback fluid data. The predicted production data is compared to the actual observed production data and the values of the unknown parameters are adjusted until the production data of the reservoir model "matches" the observed production data. The term "match" as used herein does not imply that the predicted values and the observed values match precisely. Rather, what is desirable is to minimize the standard deviation between the predicted values and the observed values. One of ordinary skill in the art with the benefit of this disclosure will be able to recognize a suitable match. Also, the predicted flowback fluid data is compared to the observed flowback fluid data. If the two sets of data do not match, then the unknown parameters are further adjusted. The process of matching both the production data and the flowback fluid data is repeated until a desirable match is achieved.

In some embodiments, the fluid identity data may be used to evaluate the efficacy of a stimulation treatment and/or the resulting clean-up after a fracturing treatment. Additionally, in some embodiments, the fluid identity data may be useful in evaluating the interactions of a component in a stimulation treatment fluid with the subterranean formation. For example, in some embodiments, it may be beneficial to compare the concentration of a certain component in a fracturing fluid prior to it be introduced into a subterranean formation to the concentration recovered.

To facilitate a better understanding of the present invention, the following examples of certain aspects of some embodiments are given. In no way should the following examples be read to limit, or define, the entire scope of the invention.

EXAMPLES

A fracturing treatment was conducted using 800 barrels ("bbl") of fracturing fluid placed into an area of a subterranean zone that was approximately 135 feet thick at a depth of approximately 12,000 feet. The fracturing fluid composition comprised approximately 0.55 M chloride, 0.115 M partially de-polymerized hydroxypropylguar (HPG), and 405 mg/L of boron as crosslinker. The tubing was displaced with approximately 307 bbl of fluid comprising 0.38 M chloride and 0.047 M partially de-polymerized hydroxypropylguar (HPG), with no boron present. The formation brine was determined to be 0.3 M sodium chloride.

After the fracturing treatment, production from the subterranean formation was initiated and 18 flowback fluid samples were collected over a period of 3.1 days. The water production was recorded as cumulative water while the gas production was recorded as gas rate. Subsequently, fluid identity data were obtained by measuring the ionic composition of the flowback fluid samples. More specifically, the amount of chloride, HPG and boron present in the samples were measured. The fluid identity data and production data, including the production rates of the flowback fluid samples and the amount of gas produced, were input into a reservoir model. Several additional known parameters were also entered into the reservoir model. The additional parameters regarding the subterranean formation that were also input into the reservoir model are found below in Table 1.

TABLE 1

Additional Model Parameters

| | |
|---|---|
| Initial Reservoir Pressure | 9500 psi |
| Reservoir Temperature | 215° F. |
| Gas Viscosity | 0.037 centipoise ("cP") |
| Gas Density | 0.29 g/mL |
| Gas Gravity | 0.65 |
| Water Viscosity | 0.27 cP |
| Matrix Porosity | 14% |
| Matrix Abs. Permeability | 1.0 millidarcy ("md") |
| Matrix $S_w$ | 40% |
| Well Spacing | 160 acres |
| Fracture Height | 135 ft |
| Fracture Porosity | 30% |
| Forchheimer-A | 1.25 |
| Forchheimer-B | 0.50 |
| Treatment Volume | 800 bbl |
| Initial Invasion $S_w$ | 90% |
| Initial Propped Fracture $S_w$ | 90% |
| Initial Wellbore Node $S_w$ | 99% |
| Tubing Volume | 307 bbl |

The initial values for certain unknown parameters of the subterranean formation were then estimated based on the data input into the reservoir model. An estimated fracture length was determined to be 400 feet, with essentially all of the fracture propped to an average proppant concentration of 2.9 lb/ft$^2$ and an average conductivity of approximately 1500 md-ft. The subterranean formation was estimated to have a permeability of 1 millidarcy, a bottomhole pressure (BHP) of 9500 psi, a temperature of 215° F., and a water saturation of 40% based, at least in part, on pressure transient analysis, logging techniques, production matching and core testing. These estimated values were also input into the reservoir model.

Based on the input, the reservoir model then produced predicted production data and predicted flowback fluid data. Subterranean formation properties and fracture properties were then adjusted to produce a desirable match between the predicted production data and the actual production data for the cumulative gas and water production. The properties that were adjusted to obtain a desirable match are listed below in Table 2.

TABLE 2

Adjusted Parameters

| | |
|---|---|
| Matrix Gas Eff. Permeability | 0.50 md |
| Matrix Water Eff. Permeability | 0.00041 md |
| Created Fracture Length | 400 ft |
| Conductive Fracture Length | 400 ft |
| Propped Fracture Width | 0.30 inches |
| Fracture Conductivity | 1500 md-ft |
| Fracture Permeability | 60 Darcy |
| Dimensionless Conductivity ("$F_{CD}$") | 3.8 |
| Fluid Invasion Depth | 2.9 inches |

Figure 2:
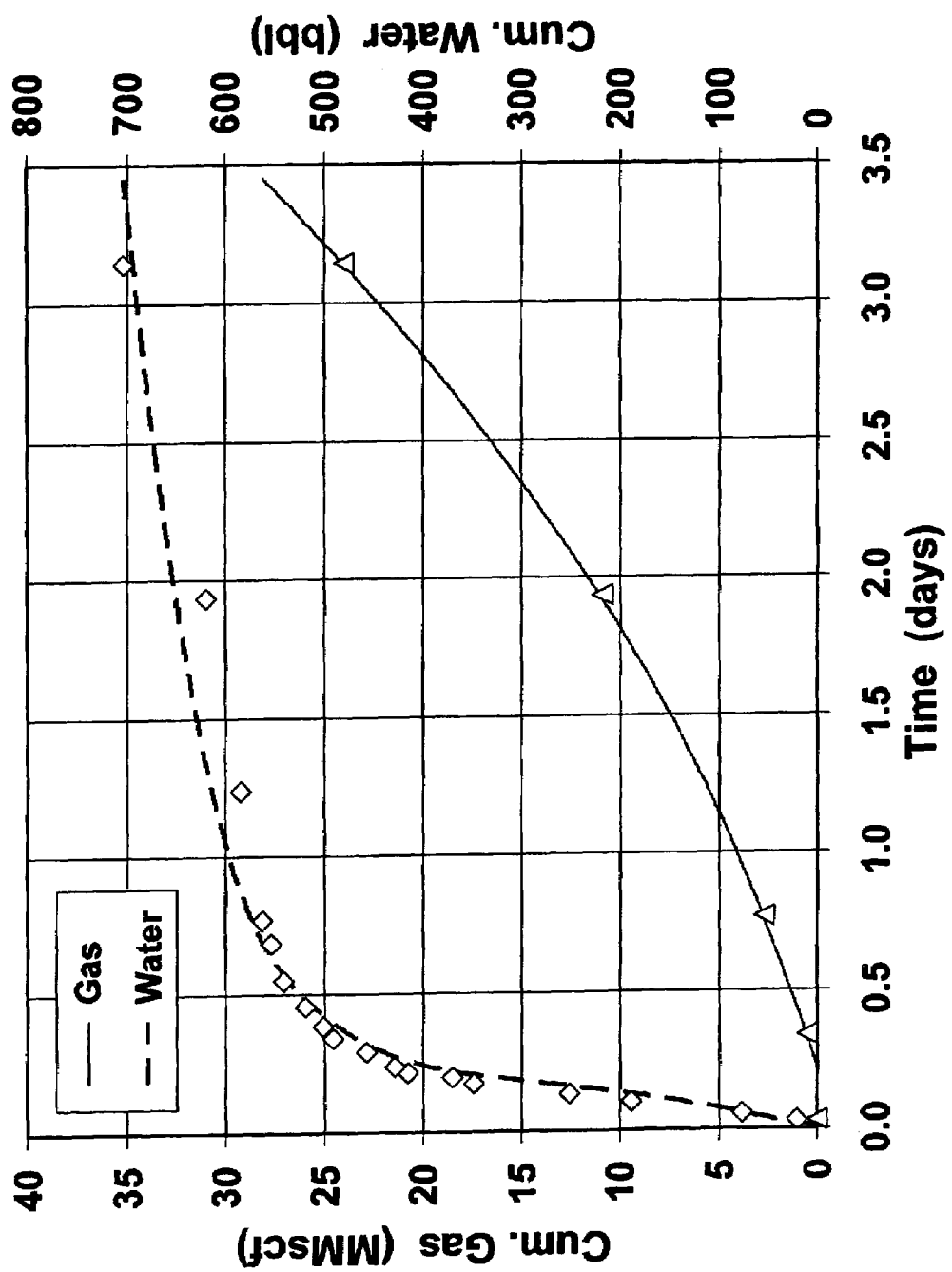
FIG. 2 is a plot of a match of production data.
Figure 3:
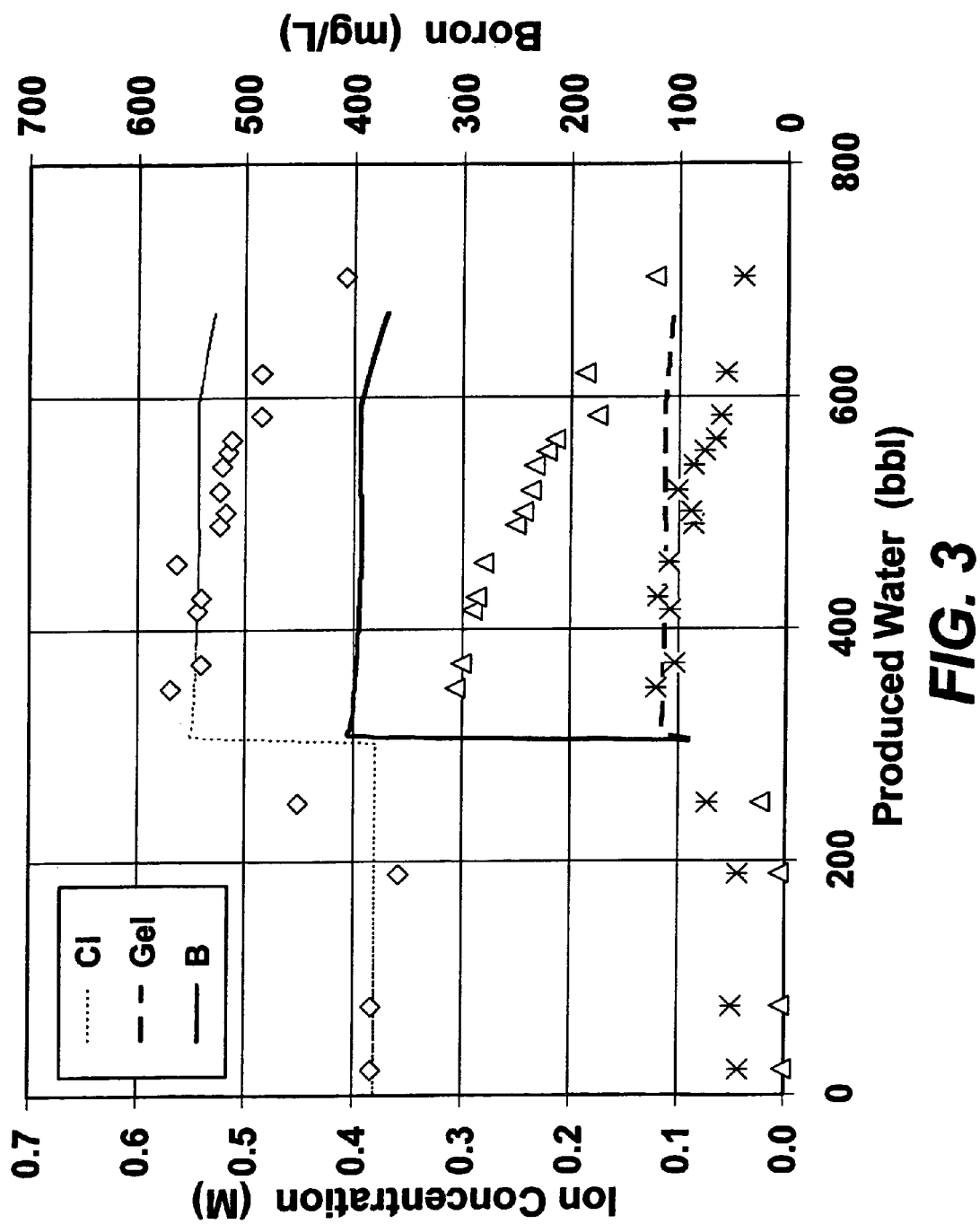
FIG. 3 is a plot of a match of fluid identity data.

Now referring to FIG. 2, it can be seen that a desirable match for the production data of water, measured in barrels ("bbl") and gas, measured in million standard cubic feet ("MMscf"), was obtained. However, in FIG. 3, it can be seen that the actual fluid identity data did not produce a desirable match with the corresponding predicted fluid identity data. That is, the predicted fluid identity data diverged from the observed fluid identity data beyond 450 bbl, suggesting that too much fracturing fluid had been returned to the surface by the simulation. Thus, the unknown parameters were further adjusted in an attempt to reduce the amount of fracturing fluid returned to the surface in order to obtain a desirable match for both the production data and the fluid identity data. These adjusted properties are listed below in Table 3.

TABLE 3

Adjusted Parameters

| | |
|---|---|
| Matrix Gas Eff. Permeability | 0.34 md |
| Matrix Water Eff. Permeability | 0.046 md |
| Created Fracture Length | 400 ft |
| Propped Length | 350 ft |
| Conductive Fracture Length | 225 ft |
| Propped Fracture Width | 0.30 inches |
| Fracture Conductivity | 1500 md-ft |
| Fracture Permeability | 60 Darcy |
| Dimensionless Conductivity ("$F_{CD}$") | 5.0 |
| Fluid Invasion Depth | 3.0 inches |

Figure 4:
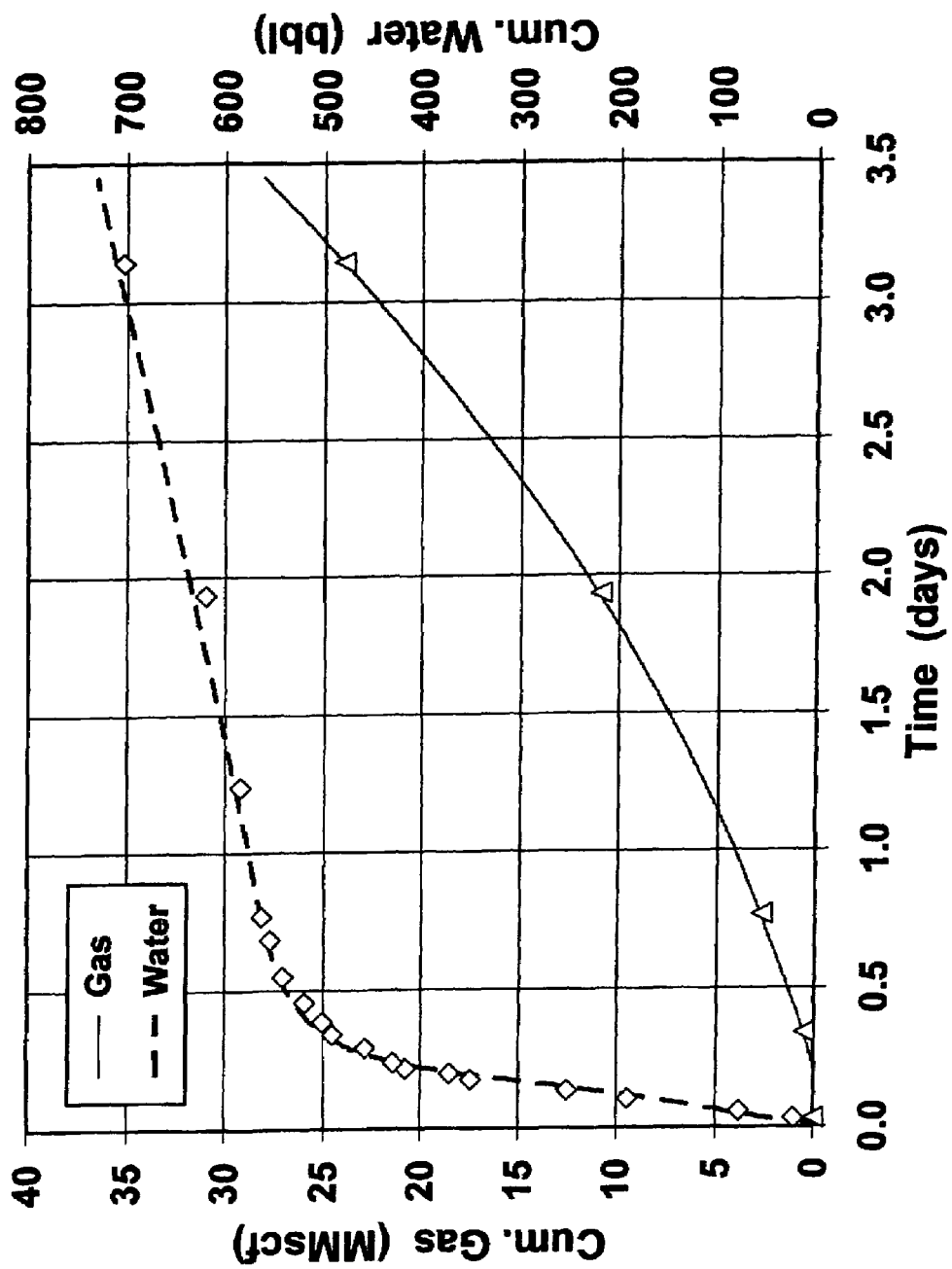
FIG. 4 is a plot of a match of production data.
Figure 5:
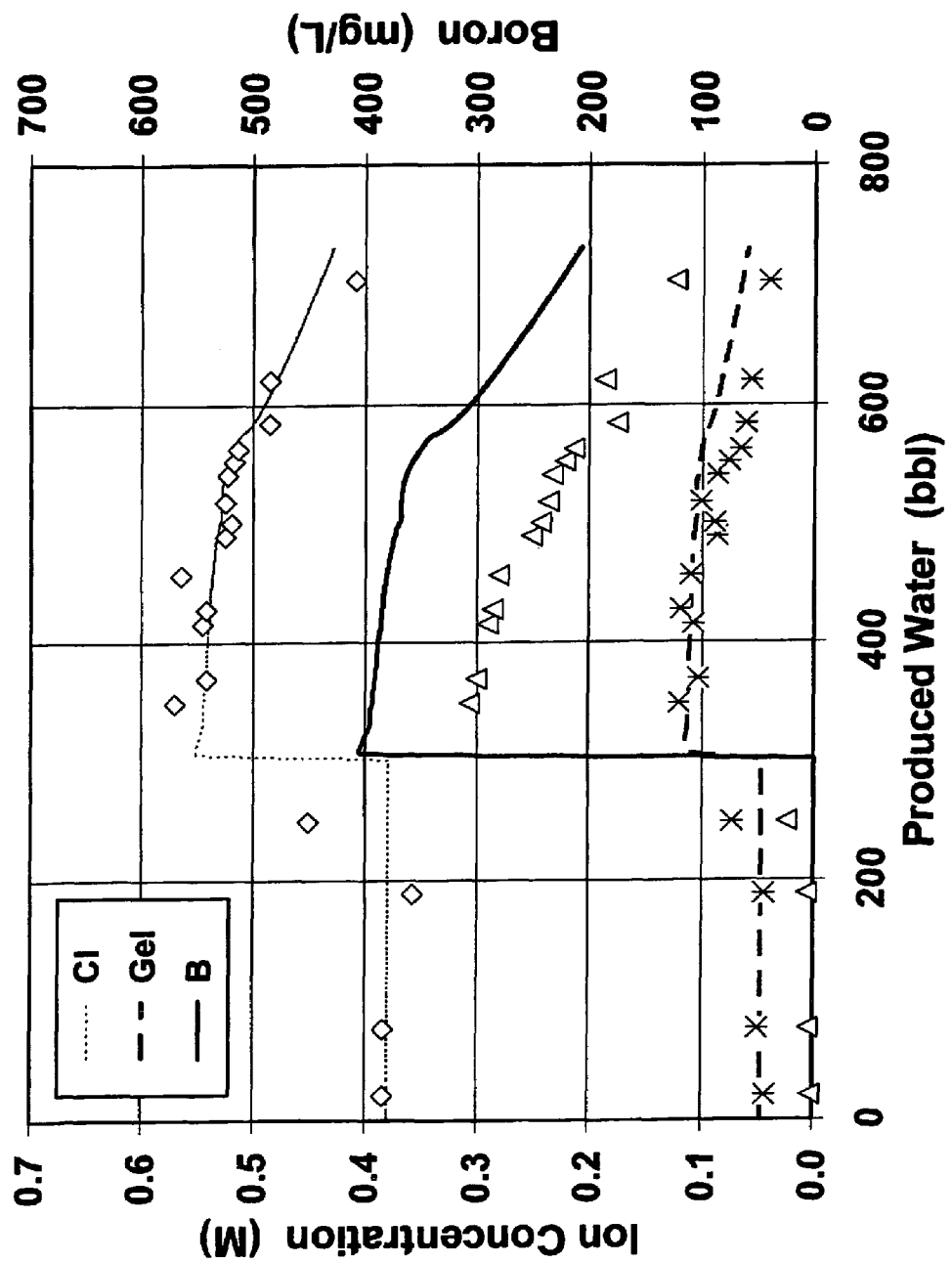
FIG. 5 is a plot of a match of fluid identity data.

Now referring to FIG. 4, it can be seen that a desirable match for the production data of water and gas was obtained. Similarly, as seen in FIG. 5, the actual fluid identity data for the gelling agent and chloride produced a desirable match with the corresponding predicted gelling agent and chloride fluid identity data. The agreement between the chloride profiles in FIG. 5 suggests that the overall recovery of fracturing fluid at the end of 3 days was well matched. The implied conductive length of 225 feet indicates that approximately 56% of the created fracture area was productive at 3 days. In this example, the predicted boron concentration did not give a reasonable match to the actual boron concentration. Instead, the flowback fluid samples appeared to contain approximately 25% less boron that expected. Thus, while the overall shape of the match was reasonable, it was significantly offset, indicating that the fate of boron may need to be further investigated.

Figure 6:
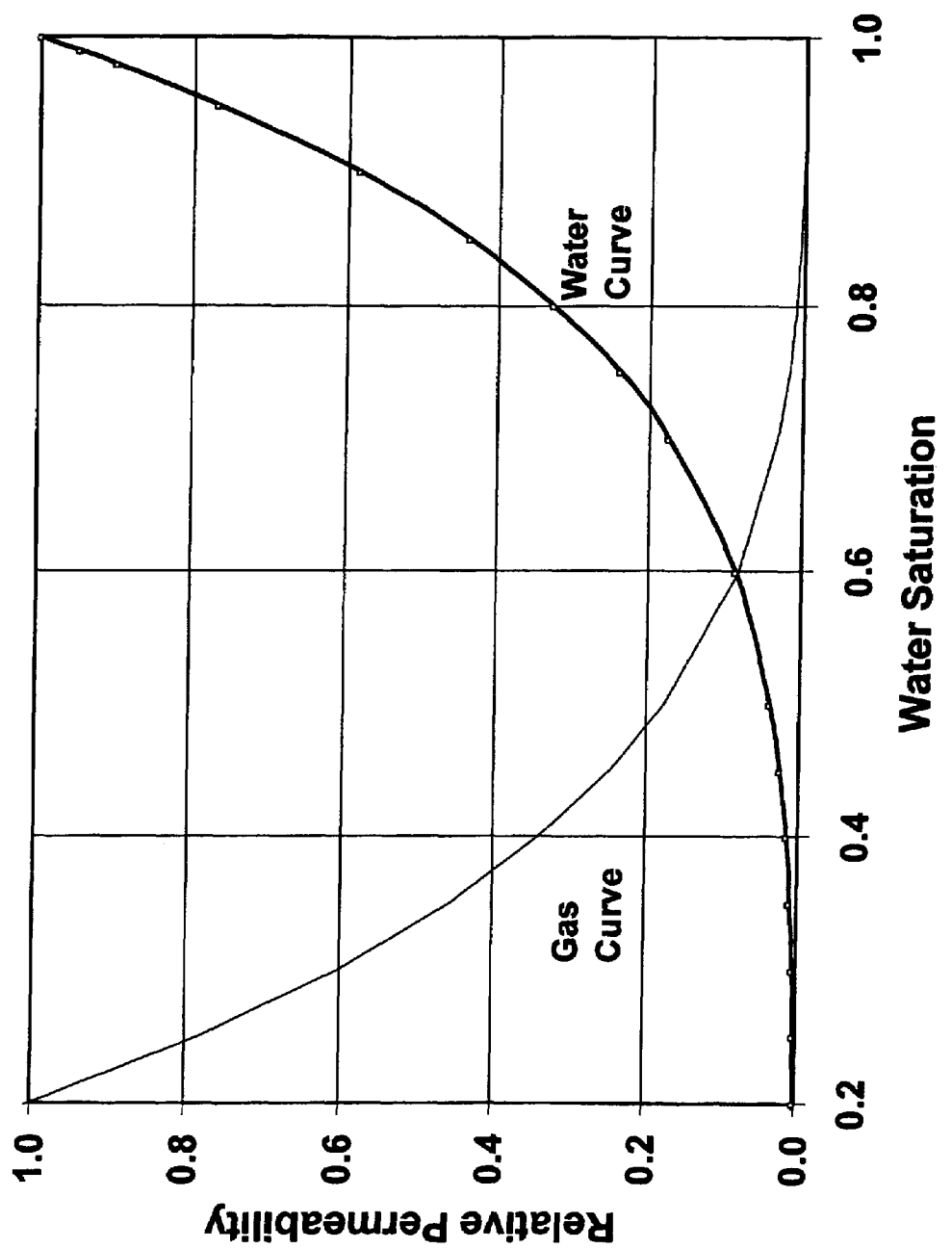
FIG. 6 is a plot of the estimated relative permeabilities to gas and water.
Figure 7:
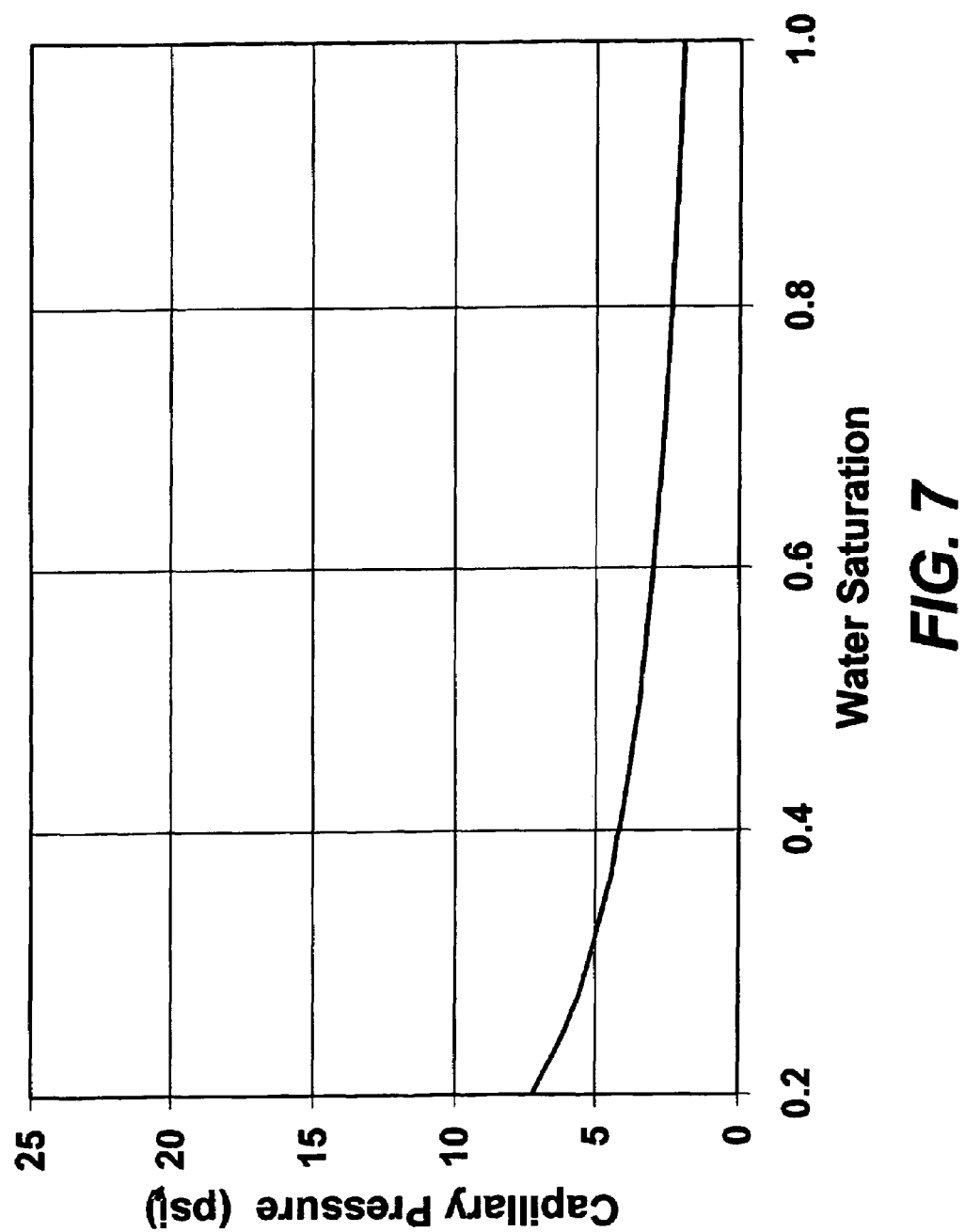
FIG. 7 is a plot of the estimated capillary pressure.
Figure 8:
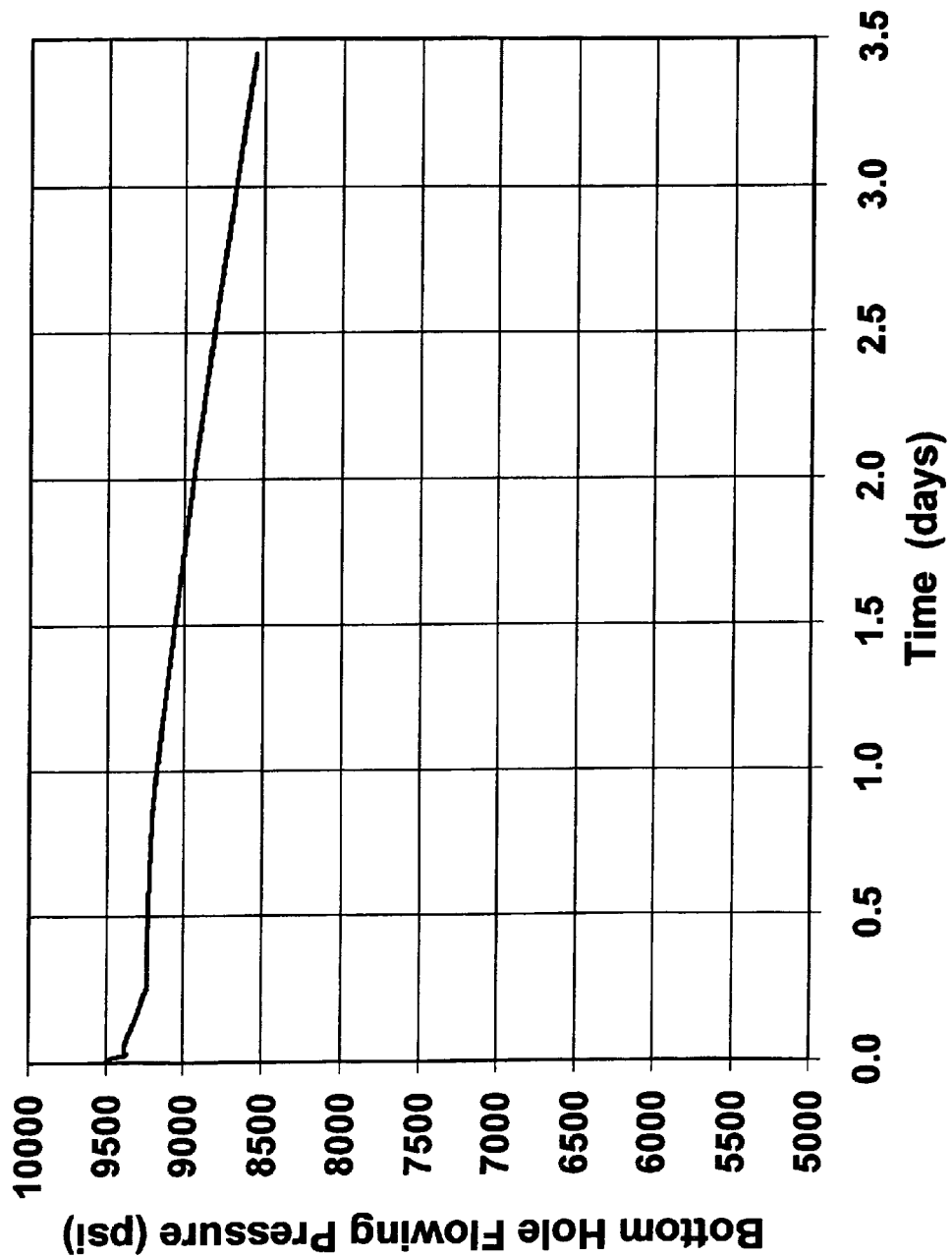
FIG. 8 is a plot of the estimated bottom hole flowing pressure.

Now referring to FIG. 6, FIG. 7, and FIG. 8 it can be seen that the relative permeability to water and gas, capillary pressure, and bottom hole flowing pressure may also be estimated using the methods of the present invention. Thus, it can be seen that for a given conductive length, there is a constrained range of estimated relative permeabilities and capillary pressures that would provide a desirable match. Furthermore, in those instances where the bottom hole flowing pressure is known, the range of possibilities may be even further constrained.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A method comprising:
   introducing a fracturing fluid into at least a portion of a subterranean formation at a pressure sufficient to create or enhance a fracture therein;
   recovering a plurality of flowback fluid samples from the subterranean formation over time;
   determining fluid identity data for the fracturing fluid and for one or more of the flowback fluid samples; and
   determining one or more approximate properties of the subterranean formation and/or fracture based, at least in part, on the fluid identity data, one or more subterranean formation properties, and at least one reservoir model.

2. The method of claim 1 wherein the fracturing fluid comprises a tracer.

3. The method of claim 2 wherein the tracer is selected from the group consisting of a flourescein dye, an oil soluble dye, an oil dispersible dye, an organic material, a phosphorescent pigment, a fluorescent pigment, a photoluminescent pigment, an oil dispersible pigment, a radioactive material, a metal, a salt, and a combination or derivative thereof.

4. The method of claim 1 wherein determining fluid identity data for one or more of the fluid flowback samples comprises analyzing the fluid flowback sample to determine the presence, absence and/or concentration of an analyte.

5. The method of claim 4 wherein the analyte is selected from the group consisting of an ion, chemical, metal, soluble material, organic material, tracer, and a combination or derivative thereof.

6. The method of claim 4 wherein analyzing the fluid flowback sample comprises using at least one of the following: atomic absorption spectroscopy, inductively coupled plasma emission spectroscopy, silver nitrate titration, infrared spectroscopy, nuclear magnetic resonance, ultraviolet spectroscopy, x-ray spectroscopy, visible spectroscopy, ion chromatography, and gas chromatography.

7. The method of claim 1 wherein the reservoir model is a numerical reservoir simulator.

8. The method of claim 1 wherein determining one or more approximate properties of the subterranean formation and/or fracture comprises:
   inputting the fluid identity data and a value for one or more subterranean formation properties into the reservoir model so as to obtain predicted flowback fluid data; and
   adjusting the value for one or more subterranean formation properties until a match is obtained between the fluid identity data and the predicted flowback fluid data.

9. The method of claim 8 further comprising:
   determining production data for the flowback fluid samples;
   inputting the fluid identity data and a value for one or more subterranean formation properties into the reservoir model so as to obtain predicted production data; and
   adjusting the value for one or more subterranean formation properties until a match is obtained between the production data and the predicted production data.

10. The method of claim 1 wherein the approximate property of the subterranean formation and/or fracture is selected from the group consisting of relative permeability, capillary pressure, effective fracture length, fracture conductivity, and fracture porosity.

11. A method comprising:
    recovering a plurality of flowback fluid samples from a subterranean formation over time;
    determining fluid identity data for one or more of the flowback fluid samples; and
    determining one or more approximate properties of the subterranean formation and/or a fracture therein based, at least in part, on the fluid identity data, one or more subterranean formation properties, and at least one reservoir model.

12. The method of claim 11 wherein determining fluid identity data for one or more of the fluid flowback samples comprises analyzing the fluid flowback sample to determine the presence, absence and/or concentration of an analyte.

13. The method of claim 12 wherein the analyte is selected from the group consisting of an ion, chemical, metal, soluble material, organic material, tracer, and a combination or derivative thereof.

14. The method of claim 11 wherein the reservoir model is a numerical reservoir simulator.

15. The method of claim 11 wherein determining one or more approximate properties of the subterranean formation and/or fracture comprises:
    inputting the fluid identity data and a value for one or more subterranean formation properties into the reservoir model so as to obtain predicted flowback fluid data; and
    adjusting the value for one or more subterranean formation properties until a match is obtained between the fluid identity data and the predicted flowback fluid data.

16. The method of claim 11 further comprising:
    determining production data for the flowback fluid samples;
    inputting the fluid identity data and a value for one or more subterranean formation properties into the reservoir model so as to obtain predicted production data; and
    adjusting the value for one or more subterranean formation properties until a match is obtained between the production data and the predicted production data.

17. A method of determining one or more approximate properties of a subterranean formation and/or a fracture therein comprising:
    obtaining fluid identity data for a plurality of flowback fluid samples; and
    using a reservoir model, with the fluid identity data and one or more subterranean formation properties as inputs thereto, to estimate one or more properties in a subterranean formation.

18. The method of claim 17 wherein obtaining fluid identity data for one or more of the fluid flowback samples comprises analyzing the fluid flowback sample to determine the presence, absence and/or concentration of an analyte.

19. The method of claim 17 wherein the reservoir model is a numerical reservoir simulator.

20. The method of claim 17 wherein using a reservoir model to estimate one or more properties in a subterranean formation comprises:
    determining production data for the flowback fluid samples;
    inputting the fluid identity data and a value for one or more subterranean formation properties into the reservoir model so as to obtain predicted flowback fluid data and predicted production data; and
    adjusting the value for one or more subterranean formation properties until a match is obtained between the fluid identity data and the predicted flowback fluid data, and between the production data and the predicted production data.

* * * * *

UNITED STATES PATENT AND TRADEMARK OFFICE
CERTIFICATE OF CORRECTION

PATENT NO. : 7,472,748 B2  Page 1 of 1
APPLICATION NO. : 11/607254
DATED : January 6, 2009
INVENTOR(S) : Rick D. Gdanski and Jimmie D. Weaver It is certified that error appears in the above-identified patent and that said Letters Patent is hereby corrected as shown below:

Claim 3, column 11, line 20

After "from the group consisting of a", insert --fluorescein-- and delete "flourescein".

Signed and Sealed this

Twenty-sixth Day of May, 2009

JOHN DOLL
*Acting Director of the United States Patent and Trademark Office*